(12) United States Patent
Marbach

(10) Patent No.: US 6,629,041 B1
(45) Date of Patent: Sep. 30, 2003

(54) METHODS TO SIGNIFICANTLY REDUCE THE CALIBRATION COST OF MULTICHANNEL MEASUREMENT INSTRUMENTS

(76) Inventor: Ralf Marbach, Kangasrinne 14, 90240 Oulu (FI)

( * ) Notice: Subject to any disclaimer, the term of this patent is extended or adjusted under 35 U.S.C. 154(b) by 37 days.

(21) Appl. No.: 09/829,957

(22) Filed: Apr. 11, 2001

Related U.S. Application Data

(60) Provisional application No. 60/199,726, filed on Apr. 14, 2000.

(51) Int. Cl.$^7$ ............................ G01N 31/00; G06F 19/00
(52) U.S. Cl. .............................. 702/30; 702/23; 702/70; 702/185; 702/189; 702/190; 702/191; 250/252.1
(58) Field of Search ............................ 702/23, 30, 185, 702/189, 190, 191, 70; 250/339.09, 252.1, 339.12

(56) References Cited

U.S. PATENT DOCUMENTS

| | | | | | |
|---|---|---|---|---|---|
| 5,680,321 | A | * | 10/1997 | Helmer et al. | ................. 702/30 |
| 5,724,268 | A | * | 3/1998 | Sodickson et al. | ............. 702/23 |
| 6,157,041 | A | * | 12/2000 | Thomas et al. | .............. 250/573 |
| 6,341,257 | B1 | * | 1/2002 | Haaland | ....................... 702/27 |
| 6,415,233 | B1 | * | 7/2002 | Haaland | ....................... 702/22 |

* cited by examiner

*Primary Examiner*—John Barlow
*Assistant Examiner*—Anthony T. Dougherty

(57) ABSTRACT

The prior art knows two different approaches to calibration of multichannel instruments, viz., the so-called physical and statistical calibration methods. The new methods translate the difficult inverse-problem posed by the statistical method into simpler, forward-problem, "physical" measurements of the signal and the noise. The new methods combine the quality of the statistical method with the low cost and interpretability of the physical method. The new methods disclose how to compute the optimal regression vector; how to update the optimal regression vector to account for small changes in the noise; how to choose a "good" subset of channels for measurement; and how to quantify the noise contributions from the multichannel measurement and from the reference measurement individually. The new methods are adapted to different situations to enable users in different situations to realize maximum cost savings.

19 Claims, No Drawings

METHODS TO SIGNIFICANTLY REDUCE THE CALIBRATION COST OF MULTICHANNEL MEASUREMENT INSTRUMENTS

CROSS-REFERENCE TO RELATED APPLICATIONS

This application claims the benefit of Provisional Patent Application Ser. No. 60/199,726 filed Apr. 14, 2000.

FEDERALLY SPONSORED RESEARCH—not applicable

SEQUENCE LISTING OR PROGRAM—not applicable

DRAWINGS—not applicable

SEQUENCE LISTING—not applicable

REFERENCES CITED

1. R. Marbach and H. M. Heise, *Calibration Modeling by Partial Least-Squares and Principal Component Regression and its Optimization Using an Improved Leverage Correction for Prediction Testing,* Chemometrics and Intelligent Laboratory Systems 9, 45–63 (1990)
2. R. Marbach, *On Wiener Filtering and the Physics Behind Statistical Modeling,* Journal of Biomedical Optics 7, 130–147 (January 2002)
3. T. W. Anderson, *Asymptotic theory for principal component analysis,* Ann. Math. Statist. 34, 122–148 (1963)

FIELD OF THE INVENTION

The invention relates to methods for calibrating multichannel measurement instruments.

BACKGROUND OF THE INVENTION

Multichannel instruments are instruments that measure a set of multiple input signals first, and then use an algorithm to generate a desired single output number from the measured values. The input signals can be from one multidimensional measurement, e.g., light absorbance values at different optical wavelengths, or from several one-dimensional measurements, e.g., the input set of [temperature, pressure, humidity]; or from any combination of these two. Multichannel instruments are used in many different industries and for many different applications, under varying names. They may also be called, e.g., "multivariate" or "multidimensional" or "multiple parameter" or "multi-pixel" or "broad spectrum" or "large-area" etc. The common characteristic is that the instruments must be calibrated before use, i.e., an algorithm must be programmed into the instruments that translates the multiple measured numbers into the desired single output number. Calibration is the process of determining that algorithm.

Today's procedures for calibrating multichannel instruments are ineffective and inefficient. The prior art knows two different approaches, viz., the so-called physical and statistical calibration methods, which so far have been thought of as separate and not interrelated (a summary is given, e.g., in Reference [1]). The mathematical tools used in the two approaches are similar, because both are based on linear regression techniques, but the methods differ substantially in the type and amount of data that the user has to measure in order to perform the calibration. The physical method is relatively cheap and intuitively easy to understand, however, this method can only be applied in very simple measurement situations and the quality of the result is almost always inferior to the statistical result. The statistical method is generally preferred because, in principle, it works in all cases and it converges against a desired optimal result, however, it requires large amounts of calibration data and the cost associated with collecting that data is usually very high.

At first glance it appears that, since calibration methods have been in widespread use for several decades now, the process of calibration would be fully understood and hard to improve on any further. However, much to the surprise of this author himself, this is far from true and the sad reality is that large amounts of money are currently being wasted on ineffective and inefficient procedures to find good multichannel algorithms.

The majority of the procedures in use today are based on the statistical approach, which works as follows. During a dedicated calibration time period the instrument is used as intended in the later measurement application and a large number of data points are measured and saved into memory. If the instrument measures, say, k channels, then each data point consists of (k+1)-many numbers, namely the k channel readings plus the "true" value of the desired output. The "true" value is measured using an independent reference instrument that serves as a standard to the calibration. Eventually, after a sufficient number of data points have been collected, a hyper-plane is fitted through the data points using standard linear regression techniques and the parameters of the fit are used to program the algorithm. With the advent of the personal computer, activity on the subject has increased to vast proportions and has even spawned several new branches of science, e.g., "biometrics," "econometrics," or "chemometrics;" along with about a dozen new scientific journals, a dozen new research institutes, scores of university chairs, and thousands of professionals graduated in the field.

The statistical approach works but has significant disadvantages, including:
1. Calibration time periods are often excessively long in order to model all the noise that the instrument is likely to see in future use; this is especially true in high-precision applications where low-frequency noises with time constants on the order of days, weeks or even months must be modeled;
2. the calibration data set is often affected by a dangerous effect called "spurious correlation" (discussed below) which can render results useless and can be difficult to detect;
3. there is no way to effectively use a-priori knowledge about the physics of the measurement process to ease the task of calibration; instead, the calibration is purely "statistical" and always starts from scratch;
4. there is no way to effectively and quantitatively assess the effect of hardware or measurement process changes on the calibration; consequently, there is no quantitative feedback mechanism that would tell in advance, e.g., what the effect of a planned hardware change on the system performance would be; and there is also no way to easily "maintain" or update an existing calibration to slight changes in the instrument hardware or measurement process;
5. there is no way to easily "re-use" an existing calibration for a new but similar application;
6. there are severe marketing problems because the results of statistical calibration are hard to interpret which, in turn, makes end users reluctant to buy, and depend on, a machine the inner workings of which they do not fully understand.

The reason behind all of these problems is that there is currently no understanding about the relationship between the statistical calibration process and the underlying physics of the measurement problem. As a result, even in the best case when enough effort has been spent and the statistical method has actually converged against the desired optimum result, users are still left in a situation where there is always, a feeling of distrust against the solution because it is not physically understood ("Will it really continue to work in the future?") and a feeling that one should have collected even more data ("Could I get better than this?").

The reason for the widespread use of the statistical approach, in spite of all the problems listed above, is simply that for many measurement problems there is no alternative. Also, there is the generally accepted fact that, if enough calibration data can be collected, then the statistical method somehow converges against an optimal result that can not be outperformed by other solutions. In some simple measurement situations, users shy away from the statistical approach and instead apply the so-called physical approach to calibration. In this method, the user tries to identify the multidimensional fingerprints of each and every physical effect in the multidimensional data space, one effect at a time, and then reconstruct each measured set of input signals as a weighted sum of the individual effects. Unfortunately, the physical approach only works in very simple situations, and even then the results are inferior to those one could have gotten from the statistical approach. Worse, if the measurement problem is a complicated mixture of many physical effects (which is the principal reason why most users decide to do a multichannel measurement in the first place) the physical approach breaks down and does not work at all (see, e.g. Reference [1]).

SUMMARY

The new methods work, in short, by translating the difficult inverse-problem posed by the statistical method into simpler, forward-problem, "physical" measurements of the signal and the noise. This, in turn, allows significant reductions in the amount of data needed for calibration, while simultaneously providing full insight and interpretability of the result and consistently outperforming the quality of the statistical method. The methods disclose how to compute the optimal regression vector; how to update the optimal result to account for small changes in the noise; how to choose a "good" subset of channels for measurement; and how to quantify the noise contributions from the multichannel measurement and from the reference measurement individually. The methods are adapted to different situations, i.e., to different amounts of knowledge that the user may have about the signal and the noise. The more knowledge the user has, the more significant the savings can be.

OBJECTS AND ADVANTAGES

The object of this invention is to overcome the disadvantages of the prior art listed above. The described methods significantly reduce the cost of multichannel calibration and simultaneously deliver optimal quality, consistently outperforming the statistical method on both price and quality. The new methods combine the best of both worlds, viz., the quality of the statistical method with the low cost and interpretability of the physical method. The new methods can be applied for both calibration and calibration maintenance and are adapted to different situations, i.e., to different states of knowledge that the user may have about the signal and the noise, so that maximum cost savings can be realized in different situations.

To give just one example of the amount of money that can be saved, take the chemometrics field. This field is concerned with the calibration of instruments that measure optical spectra at multiple wavelength channels to quantify, e.g., a chemical concentration in an industrial process control application. A conservative estimate by this author is that >U.S.$ 150 million worth of R&D and non-recurring engineering expenses worldwide can be saved annually just in the chemometric process-control market segment. This figure only counts expenses-saved, i.e., potential revenue increases due to increased customer acceptance of calibration-based products are not included.

DETAILED DESCRIPTION

The following discussion will be fairly complex and will require some math. In an effort to keep it as simple and concise as possible, a real-world example from the chemometric field will be used, viz., the measurement of the cholesterol concentration in blood plasma using infrared spectroscopy. The intention here, however, is merely to be concise and to be able to assign examples of physical units to the quantities involved, viz., the cholesterol concentration is measured in [mg/dL] and the infrared spectra are measured in absorbance units [AU]. The discussion, however, is not restricted in any way to cholesterol or to infrared spectroscopy but applies to all multichannel measurement systems where input data are measured and calibrated to produce an output number. The discussion below is detailed enough to allow everybody knowledgeable in the field, whatever his particular application background may be, to readily apply the new methods to his or her application. To repeat, whenever words like, e.g., "infrared spectrum," "spectral noise," "cholesterol concentration," "cholesterol response spectrum," etc. are used in the following description or claims, they are meant to be global in application-scope and not restricted to the particular spectroscopic application chosen merely as an example for the discussion. The global meaning will always be clear from the context.

First, we need to introduce some notation. Uppercase bold letters denote matrixes (e.g. X) and lowercase bold letters denote column vectors (b). The index in $X_{(m \times k)}$ means that the matrix has m rows and k columns. The following indices will be used: m is the number of calibration samples or "spectra" and k is the number of channels or "wavelength bands" per spectrum. $X^T$ denotes the transpose; $(X^T X)^{-1}$ the inverse; $X^+$ the Moore-Penrose inverse (more details below); I the identity matrix; 1 a vector of ones, $(1, 1, 1, \ldots)^T$; 0 a vector of zeros, $(0, 0, 0, \ldots)^T$; and "a≡b" means a is equal to b by definition. Finally, when it says that the user "knows" the signal and/or the noise, what is meant is that the user can somehow obtain a quantitative estimate of the signal and/or noise, e.g., by performing measurements himself, or, by using his a-priori knowledge about the underlying physics, or, by finding results published in the literature etc. The methods described below assume that the user has to perform the individual measurements himself, and describe how to perform them. Those skilled-in-the-art know that short-cuts are available to some of the pieces of information, e.g., by searching computer data banks. The heart-of-the-matter of the methods described below is not in the "how-to-acquire" the pieces of information, but in the "how-to-use-them" to achieve the desired goal.

Next, we shortly describe the statistical method of the prior art using the notation introduced above. Assume a set of blood samples is available for calibration and that m infrared spectra with k channels each are measured (X). Simultaneously, using a clinical analysis reference method, the "true" cholesterol concentrations ($y_R$) of the blood samples are also determined. The following linear regression equation is the so-called statistical calibration model:

$$y_R = X \cdot b + e \quad \text{(Eq.1)}$$

where $y_{R(m \times l)}$ vector of cholesterol concentration references (in units of [mg/dl])

$X_{(m \times k)}$ matrix of infrared calibration spectra [AU]

$b_{(k \times l)}$ regression vector [(mg/dL)/AU]

$e_{(m \times l)}$ error vector [mg/dl]

The task is to find a solution for the regression vector or "b-vector" b which minimizes the length of the error vector e and performs well in future predictions. The standard procedure is to, first, mean-center the calibration data $$\tilde{X} = X - 1_{(m \times l)} \cdot \bar{x}^T \quad \text{(Eq.2)}$$

$$\tilde{y}_R = y_R - \bar{y}_R \quad \text{(Eq.3)}$$

where $\bar{x}$ and $\bar{y}_R$ denote the mean infrared spectrum and the mean cholesterol reference concentration, respectively; and then, second, to estimate b from the least-squares (LS) solution $$\hat{b} = \tilde{X}^+ \tilde{y}_R \quad \text{(Eq.4)}$$

In most applications, the equation $\tilde{X}^+ = (\tilde{X}^T \tilde{X})^{-1} \tilde{X}^T$ holds and can be used to compute the result. Only in cases where channels are perfect linear-combinations of each other, i.e., where channels carry 100%-redundant information, does the user have to apply more elaborate computational techniques, e.g., the singular value decomposition, to compute $\tilde{X}^+$. In practice, in an effort to reduce redundancies between the channels, many users choose to compute an orthogonal decomposition of the data $\tilde{X}$ anyway and then use only a select subset of the orthogonal factors for the inversion. Well-known methods to compute such "rank-reduced inverses" include the principal component and the partial least-squares techniques. Throughout this patent, the inversion symbol "+," e.g., in $\tilde{X}^+$, is used to designate either the exact Moore-Penrose inverse or any of the rank-reduced versions, which effectively only use the data in the selected subspace and disregard the data in the subspace orthogonal to the selected factors. Continuing, the values of the calibration fit are given by $$y_{fit} = \bar{y}_R + \tilde{X} \cdot \hat{b} \quad \text{(Eq.5)}$$

and likewise for the future prediction spectra $X_{pred}$ $$y_{pred} = \bar{y}_R + (X_{pred} - 1_{(n \times l)} \cdot \bar{x}^T) \cdot \hat{b} \quad \text{(Eq.6)}$$

where n is the number of the future prediction spectra. The statistical method described above has been used for many years and when applied to a sufficiently large calibration data set, near-optimal solutions can be produced. The trouble is that the amount of calibration data needed to converge against the desired optimal solution increases steeply when the problem becomes ill-posed, i.e., when the signal is smaller than the noise in many of the directions spanned by the spectra in the multidimensional data space (for further details see Reference [2]). (It helps to think of a spectrum as a vector in the following.) Many of the measurement problems tackled today are so complicated that calibration data sets with a sufficient number of samples are extremely hard to collect, not only because of cost constraints but also because of limitations to the length of the calibration time period.

Now, the new methods come into being from the following line of reasoning. The first crucial step is to split the calibration spectra into two parts as follows:

$$X = X_n + y \cdot g^T \quad \text{(Eq.7)}$$

where $X_{n(m \times k)}$ the matrix of spectral noise [AU];

$g_{(k \times l)}$ the cholesterol response spectrum [AU/(mg/dL)]; and $y_{(m \times l)}$ the actual cholesterol concentrations in the calibration samples [mg/dL]

After mean-centering we have:

$$\tilde{X} = \tilde{X}_n + \tilde{y} \cdot g^T \quad \text{(Eq.8)}$$

In the following, the terms $\tilde{y} \cdot g^T$ and $\tilde{X}_n$ and variations of these terms, will be referred to as the "signal" and the "noise" of the multichannel measurement, respectively. The second crucial step is to split the cholesterol reference values $\tilde{y}_R$ into two parts as follows:

$$\tilde{y}_R = S \cdot (\tilde{y} + \tilde{y}_n) \quad \text{(Eq.9)}$$

where $$S \equiv \frac{\tilde{y}^T \tilde{y}_R}{\tilde{y}^T \tilde{y}}$$

the scale factor between the actual sample concentrations and the reference concentrations (Eq.10)

$$\tilde{y}_n \equiv \frac{1}{S}\left(I - \frac{\tilde{y} \cdot \tilde{y}^T}{\tilde{y}^T \tilde{y}}\right)\tilde{y}_R$$

the "reference noise" vector [mg/dl] (Eq.11)

The third crucial step is to write the solution as follows:

$$\hat{b} = \frac{S \cdot \left\{\tilde{X}_n^T\left(I_{(m \times m)} - \frac{y \cdot y^T}{y^T y}\right)\tilde{X}_n\right\}^+ \left(g + \frac{\tilde{X}_n^T \tilde{y}}{\tilde{y}^T \tilde{y}}\right) \cdot (\tilde{y}^T \tilde{y})}{1 + (\tilde{y}^T \tilde{y}) \cdot \left(g + \frac{\tilde{X}_n^T \tilde{y}}{\tilde{y}^T \tilde{y}}\right)^T \left\{\tilde{X}_n^T\left(I - \frac{y \cdot y^T}{y^T y}\right)\tilde{X}_n\right\}^+ \left(g + \frac{\tilde{X}_n^T \tilde{y}}{\tilde{y}^T \tilde{y}}\right)} + term(\tilde{X}_n^T \tilde{y}_n) \quad \text{(Eq. 12)}$$

Eq.(12) expresses the solution of the statistical calibration process in terms of the various physical effects, viz., the cholesterol signal $\tilde{y} \cdot g^T$; the spectral noise $\tilde{X}_n$; the reference concentrations and their noise $\tilde{y}_R = S \cdot (\tilde{y} + \tilde{y}_n)$; and the spurious correlations $\tilde{X}_n^T \tilde{y}$. The second summand term $(\tilde{X}_n^T \tilde{y}_n)$ in Eq.(12) is small compared to the first summand in virtually all applications and is zero if $\tilde{X}_n^T \tilde{y}_n = 0$ (for further details see Reference [2]).

Method A—How to Determine the Optimum b-vector When (i) the Signal is Known and (ii) the Noise is Known Eq.(12) contains all the adverse effects that the user is trying to get rid of in his statistical calibration process in the first place. If we now assume that the user has succeeded in collecting enough calibration data to eliminate the effect of reference noise, $\tilde{X}_n^T \tilde{y}_n = 0$; and spurious correlations, $\tilde{X}_n^T \tilde{y} = 0$; then Eq.(12) shrinks to $$\hat{b} = S \cdot \frac{\{\tilde{X}_n^T \tilde{X}_n\}^+ g \cdot (\tilde{y}^T \tilde{y})}{1 + (\tilde{y}^T \tilde{y}) \cdot g^T \{\tilde{X}_n^T \tilde{X}_n\}^+ g} \quad \text{(Eq. 13)}$$

which is the desired optimal solution. Since we now know how to express the optimal solution as a function of the underlying physical effects, viz., signal and noise, we can now measure the signal and the noise individually in a first step and then insert these estimates into Eq.(13) to directly compute the desired optimal solution, thereby avoiding the dangerous effects of insufficient data that haunted the statistical method of the prior art. Method A is summarized in Table A and described in detail below.

TABLE A

How to determine the optimum b-vector when
(i) the signal is known and (ii) the noise is known Step A1: Determine the covariance matrix of the noise:
1. measure a set of m samples representing the multichannel noise ($X_n$);
2. mean-center the data; and
3. compute the covariance matrix $N \equiv (\tilde{X}_n^T \tilde{X}_n)/m$     Eq.(A1)

Step A2: Determine the response vector g of the component-of-interest

Step A3: Determine the signal variance $s \equiv (\tilde{y}^T \tilde{y})/m$ in the application Step A4: Determine the scale factor S in the application Step A5: Compute the optimal regression vector:

1. Compute $\hat{b} = S \cdot \dfrac{N^+ g \cdot s}{1 + s \cdot g^T N^+ g}$     Eq.(A5)

2. (Optional:) Slope-adjust to the user likes.

Step A1 is to determine the covariance matrix $N$ [AU$^2$] of the noise. Note that $N$ in Eq.(A1) is not a random quantity but is a covariance matrix of a random noise process. (The advantage of dividing variances by the number of samples, and the reason for introducing the seemingly redundant quantities $N$ and $s$ in Table A, is that the scaled variances can easily be added to, or subtracted from, each other. This is a good operating procedure that should generally be followed, and its usefulness will become clear below. Sometimes, it is preferred to divide by $(m-1)$ instead of m, but this is a minor point that can be employed in any of the described methods and will not be discussed in length here.) The good news is that estimation of the noise covariance $N$ is easier and generally requires less data than the estimation of the b-vector via the statistical calibration method of the prior art, i.e., via Eq.(4). There are two main reasons for that. First, the problem of spurious correlations, which is the major cost driver in the statistical method, is eliminated. Second, a-priori knowledge about the physics of the noise can be combined with the measured data. To give an example related to the cholesterol example, consider the case where the covariance matrix of the electronic noise of the spectroscopic instrument is known to be $\sigma^2 I_{(k \times k)}$ [Volt$^2$], where $\sigma$ is the root-mean-square variation. To a good approximation, this noise can be translated into the absorbance domain using $N_{el} \equiv (\sigma/2.303)^2 \cdot \text{diag}(\text{VoltageSpectrum}^{-2})_{(k \times k)}$ [AU$^2$] where VoltageSpectrum is the average infrared spectrum in units of [Volt] and diag( . . . ) is a diagonal matrix with the inverse squared voltages on the diagonal. The quality of the estimate $N$ in Eq.(A1) is often good with regard to the larger noise factors but may be mediocre with regard to the smallest eigenvalues, which typically are from the electronic noise and which would require more calibration data to be estimated more accurately (Reference [3]). In this situation, the estimate $N$ in step A1 could be improved, e.g., by simply adding $N_{improved} \equiv N_{Eq.(A1)} + N_{el}$, and those skilled-in-the-art of statistical estimation will be able to conceive of a number of other, more elaborate methods. In summary, the only concern that remains when determining the number of samples required for Eq.(A1) is the statistical uncertainty in the estimate itself, like with any other estimation. The complete description of what it takes to estimate the eigenvalues and eigenvectors of matrix $N$ in a statistically reliable way is given in Anderson's useful paper [3], which in practice is often reduced to the rule-of-thumb that the data set should contain at least five times as many independent samples (infrared spectra) as channels (wavelength bands).

Note that step A1 might actually be redundant in the sense that, since the noise is assumed to be known in Method A, the covariance matrix might already be computed. However, the step is given for completeness here to indicate that some action by the user may be necessary. E.g., if the noise is known by virtue of an available data set $X_n$ with m samples, then the user needs to compute $N = (\tilde{X}_n^T \tilde{X}_n)/m$ at this time. Similar redundancy statements also apply to other steps described below, but will not be repeated there.

Step A2 is to determine the response vector g of the pure component-of-interest, i.e., the response spectrum [AU/(mg/dL)] of cholesterol in this example. In practice, this is either simple, e.g., by performing an optical transmission measurement of the pure component dissolved in water; or very hard to virtually impossible, e.g., an optical diffuse reflection spectrum of a component in a sample with unknown scattering characteristics and non-uniform composition. In the latter case, Method A can not be applied but other Methods described below may be.

Step A3 is to determine the strength of the signal variance $s \equiv (\tilde{y}^T \tilde{y})/m$ [(mg/dL)$^2$] for the specific application. This step requires hardly any action by the user at all, since it usually comes directly from the input specifications. E.g., the specification may say that the sample concentrations will "vary uniformly over a range from 100–350 mg/dL;" in this example the variance can be determined as $s = (250^2)/12 = 5208$ [(mg/dL)$^2$].

Step A4 is to determine the size of the scale factor S in the specific application. In >90% of applications, this step is a trivial and the solution is $S=1$ since, e.g., the average cholesterol concentration in the blood sample measured by the multichannel instrument, is identical to the average reference concentration. Sometimes, however, the reference concentration is not measured directly off of the same sample, e.g., the blood samples might be diluted for better storage before doing the reference analyses. In such cases the difference between the samples measured by the multichannel instrument and those measured by the reference method, can to be studied and the scale factor S can be adjusted accordingly. The good news is, that the value of S can be set arbitrarily, e.g., a nominal value of S=1 can always be used, if the user decides to slope-adjust the final result (see discussion following Eq.(14) below). The reason is that the all-important shape of the b-vector is not dependent on the scale factor. The advantage of spending some effort and determining the true scale factor is merely to keep track of the underlying physics, so to speak, and to make interpretation of subsequent results a little easier.

Step A5 is to compute the optimal regression vector using Eq.(A5). At this point, the resulting b-vector can be programmed into the instrument(s) and the measurement application can start in the standard way based on Eq.(6). (Note that the estimate of $\bar{y}_R$ and $\bar{x}$ in Eq.(6) is a trivial task that will not be discussed in length here. In practice, these values are often subject to regular quality control procedures anyway.)

At this point it is convenient to define the signal-to-noise ratio of the multichannel data as $$SNR_x \equiv \sqrt{(\tilde{y}^T\tilde{y}) \cdot g^T\{\tilde{X}_n^T\tilde{X}_n\}^+ g} \quad \text{(Eq. 14)}$$

If the value of $SNR_x$ is below 5, then slope adjustment may be considered necessary by the user (Reference [2]). Slope adjustment simply means that the resulting b-vector is multiplied by a scalar, which can be defined at the user's discretion. In practice, the scalar is determined by plotting the measured results into a so-called scatter plot, which by convention shows, e.g., the cholesterol values measured by the multichannel infrared method on the y-axis versus the "true" cholesterol values measured by the reference method on the x-axis. If the data points scatter around a line with a slope that deviates from the ideal value of one, then the b-vector is multiplied by a scalar that makes the data scatter closer around the unity-slope line. The trade-off is between the total mean-square error, which is minimized at a slope lower than one, and the end-of-range accuracy, which is best at unity slope. Typical multichannel measurements have slopes between about 0.9 and 1. Slope adjustment can be used both to adjust for slope deficiencies caused by low signal-to-noise ratios and to correct for unknown scale factors S. Typical multiplication factors used to adjust for the slope deficiencies caused by low signal-to-noise ratios are in the range from about 1.1 to 1.5. If the user decides to compute the b-vector using a nominal scale factor of S=1 when, in fact, the true scale factor deviates from one, then slope adjustment can simultaneously adjust any slope deficiency caused by low SNR and correct the scale factor.

Significant advantages of method A include the facts that the amount of data needed for calibration is reduced; that the problem of spurious correlations is eliminated; and that the resulting b-vector is physically interpretable. Also, in many instances, the multichannel signal and noise can be individually measured under laboratory conditions, thereby avoiding the expensive collection of in-situ calibration samples.

Method B—How to Determine the Optimum b-vector When (i) the Signal is Known and (ii) a Mixture of Noise-plus-unknown-amount-of-signal is Known This situation occurs in practice, e.g., when a set of calibration spectra has been measured directly off an on-line process but the "true" concentration values are not yet measurable on-line (which is exactly what the multichannel measurement is supposed to do once it's calibrated). The resulting data set contains the spectral noise plus some unknown, and possibly varying, amount of signal. What may be known is the variance of the unknown signal $(\tilde{y}_c^T\tilde{y}_c)/m$ during the collection of the calibration spectra, where index c is short for "unknown-amount-of-signal-in-the-noise" but, e.g., the cholesterol concentration in each individual blood sample is unknown.

The solution is to take the measured mixture matrix $\tilde{X} = \tilde{X}_n + \tilde{y}_c \cdot g^T$ and use it as if it was noise-only, basically repeating the steps of Method A above, because $$\hat{b}_c = S \cdot \frac{\{\tilde{X}_n^T\tilde{X}_n + g \cdot (\tilde{y}_c^T\tilde{y}_c) \cdot g^T\}^+ g \cdot (\tilde{y}^T\tilde{y})}{1 + (\tilde{y}^T\tilde{y}) \cdot g^T\{\tilde{X}_n^T\tilde{X}_n + g \cdot (\tilde{y}_c^T\tilde{y}_c) \cdot g^T\}^+ g} = \quad \text{(Eq. 15)}$$

$$\frac{1 + SNR_x^2}{1 + SNR_x^2 + SNR_{x_c}^2} \cdot \hat{b}$$

is virtually identical to the desired optimum result $\hat{b}$ in Eq.(13); the only difference being due to $$SNR_{x_c} \equiv \sqrt{(\tilde{y}_c^T\tilde{y}_c) \cdot g^T\{\tilde{X}_n^T\tilde{X}_n\}^+ g} \quad \text{(Eq. 16)}$$

which is the would-be signal-to-noise ratio associated with the unknown, varying signal. The scalar in the denominator of Eq.(15) is larger than in Eq.(13), but the all-important shape of the b-vector result is unchanged. Since the magnitude of the b-vector is subject to slope-adjustment by the user anyway, $\hat{b}_c$ in practice is as valuable and as useful as $\hat{b}$. The fact that some "extra" slope-adjustment may be necessary is irrelevant in practice. The important point is that no additional information about the unknown-amount-of-signal is necessary if the user decides to slope-adjust the result. Knowledge about $(\tilde{y}_c^T\tilde{y}_c)/m$ could be used to do the "extra" slope-adjustment, however, this would be merely to keep track of the underlying physics, so to speak, and to make interpretation of results a little easier. Method B is summarized in Table B and explained in detail below.

Steps B1–B5 are virtually equivalent to steps A1–A5 above and the discussions about the individual steps there, apply again here. The only practical difference to the user is that the chance for slope-adjustment to become necessary is increased. Because the unknown amount of signal acts as another form of noise to the calibration, it is advantageous to keep, e.g., the cholesterol concentration at a constant (unknown) level during the collection of the calibration data in step B1, and to the extent that one can succeed in doing that, the difference between Method A and Method B diminishes completely.

TABLE B

How to determine the optimum b-vector when (i) the signal is known and (ii) a mixture of noise-plus-unknown-amount-of-signal is known Step B1: Determine the covariance matrix of the mixture of the noise-plus-unknown-amount-of-signal:
1. measure a set of m samples representing the multichannel noise-plus-unknown-amount-of-signal (X);
2. mean-center the data; and
3. compute the covariance matrix $N_c \equiv (\tilde{X}^T\tilde{X})/m$      Eq.(B1)

Step B2: Determine the response vector g of the component -of-interest

Step B3: Determine the signal variance $s \equiv (\tilde{y}^T\tilde{y})/m$ in the application Step B4: Determine the scale factor S in the application

TABLE B-continued

How to determine the optimum b-vector when (i) the signal is known and (ii) a mixture of noise-plus-unknown-amount-of-signal is known Step B5: Compute the optimal regression vector:

1. Compute $\hat{b}_c = S \cdot \dfrac{N_c^+ g \cdot s}{1 + s \cdot g^T N_c^+ g}$  Eq.(B5)

2. (Optional:) Slope-adjust to the user likes.

The advantage of Method B is that it makes the significant advantages of Method A available to more users, in more situations.

Method C—How to Determine the Optimum b-vector When (i) the Signal is Unknown and (ii) the Noise is Known This case can occur in practice when the shape of the response vector g is unknown, e.g., in a process control application in the food industry where infrared spectra are measured to control "taste." Numbers from, say, 0–100, may be used to describe good and bad taste but what is unknown is the mixture of the physical ingredients that make up the taste. The a-priori knowledge situation here is obviously not as good as under Method A or Method B above, but it is still much better than if both the signal and the noise were unknown. If both are unknown, then there is no way around an expensive, statistical calibration procedure, which is haunted by various dangerous effects that can only be overcome by collecting large amounts of expensive calibration data. The most dangerous effect is spurious correlations, which often is the real cost driver. Spurious correlations make the calibration look better than it really is, by wrongly classifying part of the spectral noise as signal (for details see Reference [2]). As a result, the apparent signal is too large and the apparent noise is too small. Method C solves the latter of these two halves of the spurious correlation problem. Method C is half of Method A, so to speak, in that it plugs the known variance of the noise $(\tilde{X}_n^T \tilde{X}_n)/m$ directly into Eq.(13), thereby avoiding spurious correlations affecting the noise estimate, and exposing only the signal estimate to the potential danger of spurious correlations.

To understand Method C, first note that the task of the product term $\tilde{X}^T \tilde{y}_R$ is merely to estimate the signal, and that the term converges to $$\tilde{X}^T \tilde{y}_R = S \cdot (\tilde{y}^T \tilde{y}) \cdot g \quad \text{(Eq.17)}$$

in the ideal case when enough data is collected to reduce the effects of the reference noise and the spurious correlations to zero, i.e., $\tilde{X}_n^T \tilde{y}_n = 0$ and $\tilde{X}_n^T \tilde{y} = 0$. In this case, we can also write $$\tilde{y}_R^T \tilde{X} \cdot \{\tilde{X}_n^T \tilde{X}_n\}^+ \cdot \tilde{X}^T \tilde{y}_R = (\tilde{y}_R^T \tilde{y}_R) \cdot SNR_x^2 \cdot \dfrac{SNR_y^2}{1 + SNR_y^2} \quad \text{Eq. (18)}$$

where we defined the signal-to-noise ratio of the reference method as $$SNR_y \equiv \sqrt{\dfrac{\tilde{y}^T \cdot \tilde{y}}{\tilde{y}_n^T \cdot \tilde{y}_n}} \quad \text{(Eq. 19)}$$

Method C is summarized in Table C and discussed in detail below. Step C1 is to determine the covariance matrix N of the noise and is equivalent to step A1 above, where more detail is given. Step C2 is to estimate the (scaled) response vector using the correlation technique and requires the collection of calibration data. The number of samples ($m_S$) used in step C2 can be different from the number of samples (m) used in step C1. The requirements for the collection of calibration data in step C2 are not as stringent as those that apply when performing a full statistical calibration procedure of the prior art because the data set in step C2 does not need to be representative of the multichannel noise. However, the data should contain as much signal variance as possible under the constraints of the application, and the spurious correlations should be small. An estimate of the scaled response vector is then computed using Eq.(C2).

TABLE C

How to determine the optimum b-vector when (i) the signal is unknown and (ii) the noise is known Step C1: Determine the covariance matrix of the noise:
1. Measure a set of m samples representing the multichannel noise ($X_n$);
2. mean-center the data; and
3. compute the covariance matrix $N = (\tilde{X}_n^T \tilde{X}_n)/m$    Eq.(C1)

Step C2: Estimate the scaled response vector using the correlation technique:
1. measure a set of $m_S$ calibration samples (X) and analyze their "true" concentrations using a reference method ($y_R$)
2. mean-center the data; and
3. compute the scaled response vector $j = (\tilde{X}^T \tilde{y}_R)/m_S$    Eq.(C2)

Step C3: Determine the signal-to-noise ratio $SNR_y$ of the reference method

Step C4: Compute $SNR_x^2 = \dfrac{1 + SNR_y^2}{SNR_y^2} \cdot \dfrac{j^T N^+ j}{(\tilde{y}_R^T \tilde{y}_R)/m_S}$    Eq.(C4)

Step C5: Compute the optimal regression vector:

1. Compute $\hat{b} = \dfrac{N^+ j}{1 + SNR_x^2}$    Eq.(C5)

2. (Optional:) Slope-adjust to the user likes.

Step C3 is to determine the signal-to-noise ratio $SNR_y$ of the reference method. In practice, this step can often be accomplished by just checking the specifications of the reference instrument. Alternatively, so-called "gold standards" can be measured, which are basically standards certified by a second, better reference method. Step C3 keeps track of the underlying physics, so to speak, but is not necessary if the user decides to slope-adjust the final result. In this case, a nominal value of, e.g., $SNR_y=10$, can be used. In many applications, the reference method is actually even better than $SNR_y=10$, in which case step C3 does not make much practical difference to the result anyway, because $(1+SNR_y^2)/SNR_y^2 \approx 1$ in Eq.(C4) below.

Step C4 is to compute the $SNR_x^2$, which happens to be a valuable and useful intermediary result. Eq.(C4) is a particularly useful way of computing the $SNR_x^2$ here, however, there are other ways which could be used as well, e.g., see the discussion of Eqs.(21)–(26) below. Step C4 is another step that keeps track of the underlying physics, so to speak, but is not necessary if the user decides to slope-adjust the final result. In this case, a nominal value of, e.g., $SNR_x=10$, can be used.

Step C5 is to compute the optimal b-vector using Eq.(C5) and, as always, to slope-adjust the result if so desired.

The advantage of Method C is that it reduces the danger of spurious correlations and that it eases the requirements on the calibration data set that must be collected.

Method D—How to Determine the Individual Contributions From the Noise in the Multichannel Measurement and the Noise in the Reference Measurement

In the end, the quality of a calibration is assessed by plotting the measured results into a scatter plot, which by convention shows the values measured, e.g., by the multichannel infrared method on the y-axis versus the "true" cholesterol values measured by the reference method on the x-axis. Sometimes, the reference noise in the "true" values themselves is significant. Above, we defined the signal-to-noise ratio $SNR_x$ of the multichannel measurement (Eq.(14)) and the signal-to-noise ratio $SNR_y$ of the reference measurement (Eq.(19)). Now, we also define the total SNR of the calibration as $$SNR \equiv \sqrt{\frac{SNR_x^2 \cdot SNR_y^2}{1 + SNR_x^2 + SNR_y^2}} \qquad \text{(Eq. 20)}$$

It turns out that calibration quality, however it is measured, is dependent only on the total SNR. E.g., what is often done for quality assessment is to (1) plot the measured data into a scatter plot; then (2) "bias-correct" the scatter plot by adding or subtracting a constant to the values on the y-axis, to make their average value equal to the average of the values of the x-axis; and then (3) fit a straight-line through the data points using standard least-squares techniques. Various quality measures can be read from this chart. E.g., the slope of the fitted line is $$slope \equiv \frac{\tilde{y}_{fit}^T \tilde{y}_R}{\tilde{y}_R^T \tilde{y}_R} = \frac{SNR^2}{1 + SNR^2} \qquad \text{Eq. (21)}$$

The correlation coefficient between the measured and the reference values is $$r \equiv \frac{\tilde{y}_{fit}^T \tilde{y}_R}{\sqrt{(\tilde{y}_{fit}^T \tilde{y}_{fit}) \cdot (\tilde{y}_R^T \tilde{y}_R)}} = \sqrt{\frac{SNR^2}{1 + SNR^2}} \qquad \text{Eq. (22)}$$

The slope error is $$SlopeError \equiv \sqrt{(\tilde{y}_R - slope \cdot \tilde{y}_R)^T \cdot (\tilde{y}_R - slope \cdot \tilde{y}_R)} = \frac{\sqrt{\tilde{y}_R^T \tilde{y}_R}}{1 + SNR^2} \qquad \text{Eq. (23)}$$

The scatter error around the fitted line is $$ScatterError \equiv \sqrt{(\tilde{y}_{fit} - slope \cdot \tilde{y}_R)^T \cdot (\tilde{y}_{fit} - slope \cdot \tilde{y}_R)} = \sqrt{\tilde{y}_R^T \tilde{y}_R} \frac{SNR}{1 + SNR^2} \qquad \text{Eq. (24)}$$

The minimum mean-square error, which occurs at the slope given in Eq.(21), is $$PRESS^{\frac{1}{2}} = \sqrt{(\tilde{y}_{fit} - \tilde{y}_R)^T (\tilde{y}_{fit} - \tilde{y}_R)} = \sqrt{\tilde{y}_R^T \tilde{y}_R} \frac{1}{\sqrt{1 + SNR^2}} \qquad \text{Eq. (25)}$$

and the prediction error at "100% slope adjustment" a.k.a. unity slope is $$PRESS^{\frac{1}{2}}_{slope=1} \equiv \sqrt{\left(\frac{\tilde{y}_{fit}}{slope} - \tilde{y}_R\right)^T \left(\frac{\tilde{y}_{fit}}{slope} - \tilde{y}_R\right)} = \sqrt{\tilde{y}_R^T \tilde{y}_R} \frac{1}{SNR} \qquad \text{Eq. (26)}$$

All of the measures above depend on SNR and on SNR only, which is unfortunate, because in some situations there is a need to quantify $SNR_x$ and $SNR_y$ individually. The point here is not to improve the optimal b-vector result, which is only dependent on $SNR_x$, but rather to avoid wasting R&D money on fruitless endeavors. It may be hard to believe, but sometimes, large amounts of R&D money are wasted on efforts to improve the $SNR_x$ of instruments that, in fact, are used in applications where the total SNR is limited by the $SNR_y$ of the reference method. The reason why this can happen in practice, is that the major part of the reference noise often is not due to the inaccuracy of the reference instrument itself (which can usually be estimated) but is due to differences between the samples, or the handling of the samples, measured by the multichannel instrument and by the reference instrument. These sampling differences can sometimes be hard to detect and even harder to estimate quantitatively.

In order to determine $SNR_x$ and $SNR_y$ individually, some knowledge about the physics of the measurement process must be used. If both the spectral signal and the spectral noise are known, then the task can be accomplished as follows. First determine the $SNR_x$ using Eq.(13); then measure the total SNR of the application by using, e.g., one of the Eqs.(21) to (26); and then determine $SNR_y$ by using $$SNR_y = SNR \cdot \sqrt{\frac{1 + SNR_x^2}{SNR_x^2 - SNR^2}} \qquad \text{Eq. (27)}$$

The task is much harder when the response vector g is unknown. There is, however, one practical method that can help. Assume that two calibration data sets are collected under virtually identical experimental conditions and that the calibration results are, respectively $$SNR_I \equiv \sqrt{\frac{SNR_{x,I}^2 \cdot SNR_{y,I}^2}{1 + SNR_{x,I}^2 + SNR_{y,I}^2}} \quad \text{and}$$

$$SNR_{II} \equiv \sqrt{\frac{SNR_{x,II}^2 \cdot SNR_{y,II}^2}{1 + SNR_{x,II}^2 + SNR_{y,II}^2}} \qquad \text{Eqs. (28 I, 28 II)}$$

Now, even when the individual contributions from the spectral noise and the reference noise in the two experiments are unknown, what is often known is the ratios, i.e., the factors $k_x$ and $k_y$ defined in the equations $SNR_{x,II}^2 = k_x \cdot SNR_{x,I}^2$ and $SNR_{y,II}^2 = k_y \cdot SNR_{y,I}^2$. Method D uses this ratio information to determine the $SNR_x$ and $SNR_y$ individually. Method D is summarized in Table D and discussed in detail below.

Step D1 is to perform two "different" calibrations under virtually identical experimental conditions, where "different" means with as much difference between the factors $k_x$ and $k_y$ as possible (this will be discussed in detail below). Step D2 is to determine the total signal-to-noise ratios $SNR_I$ and $SNR_{II}$, of the two calibrations. How much a-priori knowledge the user has about the signal and the noise is irrelevant here, and even in the worst case when both the signal and the noise are unknown, the SNR's can easily be estimated, e.g., by plotting the scatter plot and using one of the equations Eq.(21)–Eq.(26). An alternative method to measure the total SNR in a situation where both the signal and the noise are unknown, is to use the identity $$\frac{\hat{b}^T \cdot \tilde{X}^T \tilde{X} \cdot \hat{b}}{\tilde{y}_R^T \tilde{y}_R} = \frac{SNR^2}{1 + SNR^2} \qquad \text{Eq. (29)}$$

which only needs the measured data $\tilde{X}$, $\tilde{y}_R$ and the result of the calibration $\hat{b}$ as inputs, and from which the total SNR can easily be determined.

TABLE D

How to determine the individual contributions from the noise in the multichannel measurement and the noise in the reference measurement Step D1: Perform two different calibrations under virtually identical experimental conditions
Step D2: Determine the total signal-to-noise ratios $SNR_I$ and $SNR_{II}$ of the two calibrations
Step D3: Determine the ratio factors $k_x$ and $k_y$
Step D4: Compute the intermediary results:

$$t_1 = 4 \cdot (k_x - 1) \cdot k_y \cdot SNR_I^2 \cdot (k_x \cdot SNR_I^2 - SNR_{II}^2) \cdot SNR_{II}^2 \qquad \text{Eq.(D4a)}$$

$$t_2 = (k_x \cdot SNR_I^2 \cdot (k_y - SNR_{II}^2) + (k_y \cdot SNR_I^2 - 1) \cdot SNR_{II}^2)^2 \qquad \text{Eq.(D4b)}$$

$$t = \sqrt{t_1 + t_2} \qquad \text{Eq.(D4c)}$$

Step D5: Compute the individual signal-to-noise-ratios as follows:

$$SNR_{x,I} = \left\{ \frac{SNR_{II}^2 + k_y \cdot SNR_I^2 \cdot SNR_{II}^2 - k_x \cdot SNR_I^2 \cdot (SNR_{II}^2 + k_y) - t}{2 \cdot k_x \cdot (k_y \cdot SNR_I^2 - SNR_{II}^2)} \right\}^{\frac{1}{2}} \qquad \text{Eq.(D5a)}$$

$$SNR_{y,I} = \left\{ \frac{SNR_{II}^2 - k_y \cdot SNR_I^2 \cdot SNR_{II}^2 + k_x \cdot SNR_I^2 \cdot (SNR_{II}^2 - k_y) + t}{2 \cdot k_y \cdot (k_x \cdot SNR_I^2 - SNR_{II}^2)} \right\}^{\frac{1}{2}} \qquad \text{Eq.(D5b)}$$

$$SNR_{x,II} = \sqrt{k_x} \cdot SNR_{x,I} \qquad \text{Eq.(D5c)}$$

$$SNR_{y,II} = \sqrt{k_y} \cdot SNR_{y,I} \qquad \text{Eq.(D5d)}$$

The crucial Step D3 is to determine the ratio factors $k_x$ and $k_y$. It is important to note that $k_x$ and $k_y$ must be different for Method D to work reliably or otherwise, numerical instability can render the equations in step D5 useless in practice. Fortunately, numerically stable cases are relatively easy to achieve in practice, e.g., $k_x \cong 2$ and $k_y \cong 0.5$ is a stable case.

There are a number of ways to achieve two "different" calibrations in practice. One particularly important way is to collect a single calibration data set and then divide this data into two sets with different amounts of signal variance, say, $s_I (\equiv (\tilde{y}_I^T \tilde{y}_I)/m_I) \cong 2 \cdot s_{II}$. In virtually all applications, this implies $k_x = s_{II}/s_I \cong 2$. The signal-to-noise ratio of the reference method, on the other hand, often increases by a smaller amount or not at all. E.g., the noise of the "wet-chemistry" method used as a reference in the cholesterol example, is known to increase with increasing cholesterol concentration, which can lead to a situation where $k_y \cong 1$, giving the desired "difference." Another cost-effective way to realize two different calibrations in practice is to divide the data from a single calibration data set, into sets that have been collected under identical experimental conditions as far as the multichannel measurement is concerned, but different conditions as far as the reference sampling is concerned. E.g., there are situations where calibration samples collected early in the morning have smaller reference noise than those collected later in the day, which might be used to realize two sets with a difference of $k_y > k_x \cong 1$. Another crude way of realizing a difference is to degrade the $SNR_y$ of one data set by simply adding computer-generated random numbers to its reference values. In summary, there are a number of ways to realize two data sets with different ratio factors $k_x$ and $k_y$ in practice, and application-specific knowledge can effectively be used here.

Step D4 is to compute some useful intermediary results and the final step D5 is to compute the individual signal-to-noise ratios, $SNR_x$ and $SNR_y$ as shown in Table D.

The main advantage of Method D is that in some applications, large amounts of R&D money can be saved. (Method D will not appear in the claims but is disclosed as a service to industry and regulatory agencies. It can be used to avoid repetition of some past blunders.)

Method E—How to Determine a "Good" Set of Channels for Measurement

As discussed above, whatever criterion is used to measure calibration quality, in the end it is only SNR that counts. In the majority of applications, the total SNR is limited by the $SNR_x$ of the multichannel measurement, which in turn increases monotonically with the number of channels used (i.e., every new, e.g., wavelength band either improves the quality or at least does not make it worse). Therefore, there is no single "optimal" wavelength range and the practical tradeoff is, in short, to find the most $SNR_x$-bang for the least hardware-buck. There is large interest in this issue but none of the methods suggested so far is useful and many are actually misleading.

In practice, when tackling a new measurement problem, it is standard procedure to perform a feasibility study first. In a typical feasibility study, data is measured using expensive "research-grade" instrumentation capable of measuring a very large number of channels. The next step is selection of a "good" subset of channels, for which dedicated instruments are then developed. Method E defines a criterion and method to guide the user through the often complicated process of making the necessary hardware tradeoffs to arrive at a "good" subset.

Method E, in short, computes the SNR, as a function of the subset of channels selected for the multichannel measurement. One major advantage is that $SNR_x$ scales linearly, i.e., $2 \times SNR_x$ is twice as good as $1 \times SNR_x$, as opposed to other commonly used quality measures, which scale in a non-linear way. Method E is summarized in Table E and described in detail below.

TABLE E

How to determine a "good" set of channels for measurement

Step E1: Using a research-grade instrument, measure a representative set of calibration samples covering a large number of channels.
Step E2: Select a subset of channels and determine the $SNR_x$ for the selected subset:
1. Select a subset of channels and perform a calibration
2. Determine the total SNR of the calibration and approximate $SNR_x \cong SNR$
3. (Optionally:) Determine the individual contributions, $SNR_x$ and $SNR_y$
Step E3: Evaluate tradeoff between $SNR_x$ and estimated cost of hardware and other marketing requirements; go back to step E2 until satisfied Step E1 is to measure a representative set of calibration samples covering a large number of channels, using a research-grade or similar instrument. The calibration samples must represent the signal and the noise of the multidimensional data. The amount of a-priori knowledge available about the signal and the noise is irrelevant for Method E although, of course, more is generally better because the task of calibration gets easier. Step E2 is to select a subset of channels for calibration and to perform a calibration, and then to determine the signal-to-noise ratio $SNR_x$ of the multichannel measurement in the selected subset. Since $SNR_y$ is much larger than $SNR_x$ in most applications, step E2 often is simply to determine the total SNR of the calibration and then to approximate $SNR_x \cong SNR$. This approximation is accurate whenever $SNR_y \geq 3 \cdot SNR_x$, approximately. The total SNR can be determined as described under step D2 above. In the rare cases that the $SNR_y$ of the reference is a limiting factor to the measured total SNR, it is necessary to estimate the value of $SNR_y$ like in step C3 above and then "subtract" it from the total SNR by using $$SNR_x = SNR \cdot \sqrt{\frac{1 + SNR_y^2}{SNR_y^2 - SNR^2}} \qquad \text{Eq. (30)}$$

Determining the values of the individual contributions $SNR_x$ and $SNR_y$ is helpful in assessing the relative importance of $SNR_x$ and $SNR_y$ and will yield a more accurate estimate of $SNR_x$. However, to repeat, in most applications the approximation $SNR_x \cong SNR$ is a very useful, accurate and linear, measure of the quality of the multichannel measurement.

Step E3 is to evaluate the tradeoff between the $SNR_x$ achieved with the selected subset of channels, versus the estimated cost of the hardware and other marketing requirements. Step E3 closes the loop of the iterative process that typically makes up the feasibility study. In practice, the process often loops back all the way to step E1 as well, which is not shown in Table E but still is within the scope of this invention.

The advantage of Method E is that it provides the user with a linear and relevant measure of the quality of the multichannel measurement.

Method F—How to Determine the Optimum b-vector When (i) the Zero-response Region of the Signal is Known and (ii) the Noise is Known This case occurs often in practice when the sampling conditions are determined by the application and are not 100% user-controlled, e.g., in optical diffuse reflection measurements on powders, webs, or tissues. Here, the shape of the response vector g in the diffuse reflection application is unknown and the cost of deducing it may be prohibitive. However, what is usually known is the spectral regions where g is zero, e.g., from a simple optical transmission measurement. This is very valuable knowledge that can be used for dramatic cost reductions. Method F, in short, reduces the statistical calibration procedure to cover just the spectral regions with non-zero response, and then adds the zero-response wavelength regions in a second step based on the new approach. (It is mentioned in passing that inclusion of zero-response channels can, and usually does, improve the quality of a multichannel calibration; this works by subtracting out noises that are correlated between the regions and is in fact the core advantage of the multichannel measurement over, say, doing multiple single-channel measurements.)

Assume that the measured channels are sorted into two groups, viz., $\tilde{X}_n = [\tilde{X}_{n,NZ} \; \tilde{X}_{n,Z}]$ with the indices meaning non-zero and zero response, respectively, and that Eq.(13) is written as $$\hat{b} = \begin{bmatrix} \hat{b}_{NZ} \\ \hat{b}_Z \end{bmatrix} = \qquad \text{(Eq. 31)}$$

$$S \cdot \frac{\begin{pmatrix} \tilde{X}_{n,NZ}^T \tilde{X}_{n,NZ} & \tilde{X}_{n,NZ}^T \tilde{X}_{n,Z} \\ \tilde{X}_{n,Z}^T \tilde{X}_{n,NZ} & \tilde{X}_{n,Z}^T \tilde{X}_{n,Z} \end{pmatrix}^+ \begin{pmatrix} g_{NZ} \\ 0 \end{pmatrix} \cdot (\tilde{y}^T \tilde{y})}{1 + (\tilde{y}^T \tilde{y}) \cdot \begin{pmatrix} g_{NZ} \\ 0 \end{pmatrix}^T \begin{pmatrix} \tilde{X}_{n,NZ}^T \tilde{X}_{n,NZ} & \tilde{X}_{n,NZ}^T \tilde{X}_{n,Z} \\ \tilde{X}_{n,Z}^T \tilde{X}_{n,NZ} & \tilde{X}_{n,Z}^T \tilde{X}_{n,Z} \end{pmatrix}^+ \begin{pmatrix} g_{NZ} \\ 0 \end{pmatrix}}$$

Since the ordering of the channels is irrelevant, Eq.(31) does not require the non-zero and zero response channels to actually be contiguous wavelength regions. Rather, the user is free to select non-zero and zero channels at his discretion and then re-order them into the two subsets NZ and Z as written in Eq.(31). For conciseness, define $G \equiv \tilde{X}_{n,NZ}^T \tilde{X}_{n,NZ}$, $C \equiv \tilde{X}_{n,Z}^T \tilde{X}_{n,NZ}$ and $Z \equiv \tilde{X}_{n,Z}^T \tilde{X}_{n,Z}$. Further define $$\hat{b}_{NZ,Short} \equiv S \cdot \frac{G^+ g_{NZ} \cdot (\tilde{y}^T \tilde{y})}{1 + (\tilde{y}^T \tilde{y}) \cdot g_{NZ}^T G^+ g_{NZ}} \qquad \text{Eq. (32)}$$

which is the optimal solution in the "short" wavelength range containing only the non-zero response channels. Also define intermediary result $D \equiv Z - C \cdot G^+ C^T$ and the signal-to-noise ratios, $SNR_{x,Short}^2 \equiv (\tilde{y}^T \tilde{y}) \cdot g_{NZ}^T G^+ g_{NZ}$ in the short range and, $\Delta SNR_x^2 \equiv (\tilde{y}^T \tilde{y}) \cdot g_{NZ}^T G^+ C^T D^+ C \cdot G^+ g_{NZ}$ the improvement due to inclusion of the zero-response region. Now, knowing the noise in the zero-response wavelength region, the short result Eq.(32) can be extended to cover a broader range of channels by using $$\begin{bmatrix} \hat{b}_{NZ} \\ \hat{b}_Z \end{bmatrix} = \frac{1 + SNR_{x,Short}^2}{1 + SNR_{x,Short}^2 + \Delta SNR_x^2} \cdot \begin{pmatrix} (I + G^+ C^T D^+ C) \cdot \hat{b}_{NZ,Short} \\ -D^+ C \cdot \hat{b}_{NZ,Short} \end{pmatrix} \qquad \text{Eq. (33)}$$

Method F is summarized in Table F and described in detail below. In the interest of consistency and to minimize chances for user errors, all variances in Table F are scaled by the number of samples.

TABLE F

How to determine the optimum b-vector when (i) the zero-response region of the signal is known and (ii) the noise is known Step F1: Determine the covariance matrix of the noise in the broad range of channels:
1. measure a set of m samples representing the multichannel noise $(X_n)$;
2. mean-center the data;
3. sort channels into two subsets with non-zero and zero response, respectively; re-order channels and re-write data matrix as $\tilde{X}_n = [\tilde{X}_{n,NZ} \; \tilde{X}_{n,Z}]$;
4. compute covariance matrix and dissect into three parts G, C, and Z as shown:

$$N \equiv \frac{\tilde{X}_n^T \tilde{X}_n}{m} = \begin{pmatrix} \frac{\tilde{X}_{n,NZ}^T \tilde{X}_{n,NZ}}{m} & \frac{\tilde{X}_{n,NZ}^T \tilde{X}_{n,Z}}{m} \\ \frac{\tilde{X}_{n,Z}^T \tilde{X}_{n,NZ}}{m} & \frac{\tilde{X}_{n,Z}^T \tilde{X}_{n,Z}}{m} \end{pmatrix} \equiv \begin{pmatrix} G & C^T \\ C & Z \end{pmatrix} \qquad \text{Eq.(F1)}$$

Step F2: Perform a calibration in the short range of channels containing only the non-zero response channels:

TABLE F-continued

How to determine the optimum b-vector when (i) the zero-response region of the signal is known and (ii) the noise is known 1. measure a set of $m_S$ calibration samples ($X_{NZ}$) and analyze their "true" concentrations using a reference method ($y_R$)
2. mean-center the data; and
3. compute the short b-vector $\hat{b}_{NZ,Short} = \tilde{X}_{NZ}{}^+ \tilde{y}_R$      Eq.(F2)

Step F3: Determine the $SNR_y$ of the reference method
Step F4: Determine the $SNR_{x,Short}$ in the short range of channels:

1. 
$$\text{Compute } t \equiv \frac{\hat{b}_{NZ,Short}^T \cdot (\tilde{X}_{NZ}^T \tilde{X}_{NZ}/m_S) \cdot \hat{b}_{NZ,Short}}{(\tilde{y}_R^T \tilde{y}_R / m_S)} \quad \text{Eq.(F4a)}$$

2. Compute $SNR_{Short} \equiv \sqrt{t/(1-t)}$      Eq.(F4b)

3. 
$$\text{Compute } SNR_{x,Short} \equiv SNR_{Short} \cdot \sqrt{\frac{1 + SNR_y^2}{SNR_y^2 - SNR_{Short}^2}} \quad \text{Eq.(F4c)}$$

Step F5: Compute intermediary result $D \equiv Z - C \cdot G^+ \cdot C^T$   Eq.(F5)
Step F6: Compute the improvement $$\Delta SNR_x^2 \equiv \frac{((1+SNR_{x,Short}^2)))^2}{(\tilde{y}_R^T \tilde{y}_R)/m_S} \cdot \frac{1 + SNR_y^2}{SNR_y^2} \cdot \hat{b}_{NZ,Short}^T C^T D^+ C \cdot \hat{b}_{NZ,Short} \quad \text{Eq.(F6)}$$

Step F7: Compute the long b-vector by extending the short b-vector over the broad range of channels:
1. Compute      Eq.(F7)

$$\begin{bmatrix} \hat{b}_{NZ} \\ \hat{b}_Z \end{bmatrix} = \frac{1 + SNR_{x,Short}^2}{1 + SNR_{x,Short}^2 + \Delta SNR_x^2} \cdot \begin{pmatrix} (I + G^+ C^T D^+ C) \cdot \hat{b}_{NZ,Short} \\ -D^+ C \cdot \hat{b}_{NZ,Short} \end{pmatrix}$$

2. (Optional:) Slope-adjust to the user likes.

Step F1 is to determine the covariance matrix of the noise in the broad range of channels. This step is virtually identical to step A1 above, except that the channels are re-ordered into two groups, viz., group "NZ" with non-zero signal and group "Z" with zero signal. The resulting matrix is split into three parts, viz., G the covariance matrix of the channels with non-zero response, Z the covariance matrix of the channels with zero response, and C the cross covariance matrix between the two regions.

Step F2 is to perform a calibration in the "short" range of channels containing only the non-zero response channels, with the goal of computing the "short" b-vector $\hat{b}_{NZ,Short}$. There are several ways to accomplish this goal. First of all, for many users, step F2 may actually be redundant in the sense that the short b-vector may already be available from a past calibration. Second, Method C can be used advantageously here to compute $\hat{b}_{NZ,Short}$. In the interest of generality and conciseness, Step F2 in Table F describes the case where a full statistical calibration procedure is performed by the user, which can include all the tricks-of-the-trade useful when performing statistical calibrations like, e.g., outlier detection or orthogonal factor selection. As soon as the user has produced what he thinks is the best result within the short wavelength region, he can proceed to step F3.

Step F3 is to determine the $SNR_y$ of the reference method and is virtually equivalent to step C3 above. Step F4 is to determine the $SNR_{x,Short}$ of the multichannel measurement in the short range of channels, and is virtually equivalent to what was done in step E2 above. Step F5 is to compute a useful intermediary result and step F6 is to compute the improvement $\Delta SNR_x$ due to the inclusion of the zero-response channels. Steps F3, F4, and F6 are not necessary if the user decides to slope-adjust the final result, in which case nominal values can be used, e.g., $SNR_y=10$, $SNR_{x,Short}=10$, and $\Delta SNR_x=0$.

The crucial step F7 is to compute the long b-vector by extending the short b-vector over the broad channel range using Eq.(F7). As always, the long b-vector result can be slope-adjusted if so desired.

The practical advantages of Method F are enormous. Since the cost of statistical calibrations is driven by the number of calibration samples, which in turn is driven by the number of channels wanted by the user, Method F amounts to huge savings. In many applications, Method F can provide >80% of the savings that would be possible if the signal was fully known.

Method G—How to Update an Existing b-vector When the Noise Changes by a Known Amount and (i) the Signal is Unknown and (ii) the Noise is Unknown This method is important in many instances. E.g., imagine a single instrument has been calibrated to a process and the task is to transfer this calibration to other instruments. One way to do this is to measure the instrument-to-instrument differences in the lab and on an average sample, then "harden" the existing calibration by adding the instrument-to-instrument variations as another form of spectral noise. In other instances, it is necessary to assess the effect of a reduction in the noise variance, e.g., when a particular improvement to the instrument hardware is planned. Method G can be applied to both noise increases and decreases.

It is well known that variances from independent noise processes add linearly. So when the noise variance matrix N is known, it is obviously simple to add, or subtract, a known amount of noise variance Λ to the existing noise variance and then compute an updated b-vector result using, e.g., Eq.(A5) with $N_{update}=N\pm\Lambda$. What is surprising, however, is the good news that the same straightforward procedure can also be applied in the case where both the signal and the noise are unknown, i.e., when the statistical method has to be used to compute the b-vector. In this situation, the updated result can be computed by using $$\hat{b} = \left(\frac{\tilde{X}^T \tilde{X}}{m} \pm \Lambda\right)^+ \tilde{X}^T \frac{\tilde{y}_R}{m} \quad \text{Eq. (34)}$$

where Λ is the known amount of change in the noise variance, and the "+" and "−" sign are used to add or subtract noise variance, respectively. In the calibration transfer example above, the average spectra $X_{av}$ from, say, 10 different instruments may have been measured and the covariance matrix of the additional noise estimated as $\Lambda=(\tilde{X}_{av}{}^T \tilde{X}_{av})/10$. Method G is summarized in Table G and is described in detail below.

TABLE G

How to update an existing b-vector when the noise changes by a known amount and (i) the signal is unknown and (ii) the noise is unknown Step G1: Determine the covariance matrix Λ of the change in the noise
Step G2: Determine covariance terms of the existing, mean-centered calibration samples:

$$N_S \equiv \frac{\tilde{X}^T \tilde{X}}{m} \quad \text{Eq.(G2a)}$$

$$j \equiv \frac{\tilde{X}^T \tilde{y}_R}{m} \quad \text{Eq.(G2b)}$$

Step G3: Compute the updated b-vector:
1. Compute $\hat{b} = (N_S \pm \Lambda)^+ j$      Eq.(G3)
2. (Optional:) Slope-adjust to the user likes.

Step G1 is to determine the covariance matrix Λ of the change in the noise. This step might be redundant in the sense that, since the change in the noise is assumed to be known for this method, the covariance matrix may already be computed. The step is given for completeness here, e.g., if the change in the noise is known by virtue of a data set $X_{av}$, then the user needs to compute its covariance matrix Λ at this time. Step G2 is to determine the covariance terms of the existing calibration samples using Eqs.(G2a) and (G2b). Again, since the data $\tilde{X}=\tilde{X}_n+\tilde{y}\cdot g^T$ and $\tilde{y}_R$ are assumed to be available from a past statistical calibration procedure, the results $N_s$ and j may already be available. One important point in steps G1 and G2 is to avoid scaling errors associated with the different number of samples used to estimate the different variance terms, and this is why it is best to immediately divide all variances by the number of samples (or the number of samples minus one) before adding or subtracting. Step G3 is to compute the updated b-vector result using Eq.(G3) and to slope-adjust if so desired. Other steps, not shown in Table G, might follow, e.g., to determine the $SNR_x$ of the updated calibration and evaluate against the associated hardware cost of a potential hardware improvement.

The advantage of Method G is that it enables the user to quantitatively assess and incorporate into a calibration the effect of known changes in the noise even in a situation where both the signal and the noise are unknown.

The methods disclosed provide a tool set that can be used to re-define industry practices and realize significant cost savings. Variations, modifications, and combinations falling within the scope of the appended claims will be apparent to those skilled in the art. In particular, users can combine several of the methods to fit their particular needs. E.g., in a situation where (i) the zero-response region of the signal is known and (ii) a mixture of noise-plus-unknown-amount-of-signal is known; it is obviously possible to apply Method B to compute the short b-vector in step F2 and then apply Method F to extend it over the broader range of channels. Or, Method C could be used to compute the short b-vector and then extend it using Method F. Or, Method D could be used in step E2 of Method E to determine the $SNR_x$ and $SNR_y$ individually, etc.

I claim:

1. A method to calibrate a multichannel measurement instrument, comprising the steps of:
   a) determining a first estimate of the covariance matrix N of the multichannel noise;
   b) determining a second estimate of the response vector g of the component-of-interest;
   c) determining a third estimate of the signal variance s;
   d) determining a fourth estimate of the scale factor S between the sample concentrations and the reference concentrations;
   e) computing the b-vector from said estimates by using formula $$\hat{b} = S \cdot \frac{N^+ g \cdot s}{1 + s \cdot g^T N^+ g}$$

or a substantially equivalent expression;
   f) programming said b-vector into said multichannel measurement instrument and using said b-vector to predict;

whereby the detrimental effects of spurious correlation and reference noise are eliminated; the quality of the calibration is increased; the cost of the calibration process is substantially decreased; specificity to the component-of-interest is guaranteed; the calibration process is made transparent and adaptable to changes in the measurement environment; and opportunities for important system-level tradeoffs are created.

2. The method of claim 1, further including the step of slope-adjusting said b-vector.

3. The method of claim 1, wherein the step of determining said first estimate includes
   a) measuring a plurality of samples representing the multichannel noise;
   b) computing the covariance matrix of said samples.

4. The method of claim 1 wherein the step of determining said second estimate is selected from the group consisting of measuring said response vector and determining said response vector from a data base.

5. The method of claim 1 wherein at least one estimate selected from the group consisting of said third estimate and said forth estimate is determined as a nominal value.

6. The method of claim 5, further including the step of slope-adjusting said b-vector to compensate for the effect of said nominal values.

7. The method of claim 1 wherein said second estimate is determined by using the correlation technique whereby most of the advantages of the method of claim 1 can be realized in a situation where said response vector can not easily be determined otherwise.

8. The method of claim 7 wherein said multichannel measurement instrument is an optical diffuse reflection instrument.

9. The method of claim 1 wherein said multichannel noise contains an unknown and possibly varying amount of signal whereby the advantages of the method of claim 1 can be realized in a situation where the estimate of the noise is affected by unknown amounts of signal.

10. The method of claim 9, further including the step of slope-adjusting said b-vector to compensate for the effect of the unknown amount of signal.

11. The method of claim 1, wherein said multichannel measurement instrument is a spectroscopic instrument.

12. The method of claim 11, wherein said spectroscopic instrument is used in an industrial process control application.

13. The method of claim 11, wherein said spectroscopic instrument is used in a biomedical application.

14. A method to calibrate a multichannel measurement instrument in a situation where the zero-response region of the signal is known, comprising the steps of:
   a) determining a first estimate of the covariance matrix $$\begin{pmatrix} G & C^T \\ C & Z \end{pmatrix}$$

of the multichannel noise in a broad range of channels;
   b) performing a calibration in a short range of channels containing only the non-zero response channels, thereby producing a short b-vector $\hat{b}_{NZ,Short}$
   c) determining a second estimate of the signal-to-noise ratio $SNR_y$ of the reference method;
   d) determining a third estimate of the signal-to-noise ratio $SNR_{x,Short}$ of the multichannel measurement in said short range of channels;
   e) determining a forth estimate of the signal-to-noise improvement $\Delta SNR_x$;
   f) computing the long b-vector from said short b-vector and said estimates by using formula $$\begin{bmatrix} \hat{b}_{NZ} \\ \hat{b}_{Z} \end{bmatrix} = \frac{1 + SNR_{x,Short}^2}{1 + SNR_{x,Short}^2 + \Delta SNR_x^2} \cdot \begin{pmatrix} (I + G^+ C^T D^+ C) \cdot \hat{b}_{NZ,Short} \\ -D^+ C \cdot \hat{b}_{NZ,Short} \end{pmatrix}$$

or as substantially equivalent expression;

g) programming said long b-vector into said multichannel measurement instrument and using said long b-vector to predict;

whereby further substantial cost advantages are provided.

15. The method of claim 14, further including the step of slope-adjusting said long b-vector.

16. The method of claim 14 wherein at least one estimate selected from the group consisting of said second estimate, said third estimate, and said forth estimate is determined as a nominal value.

17. The method of claim 16, further including the step of slope-adjusting said long b-vector to compensate for the effect of said nominal values.

18. A method of updating an existing b-vector to account for a known amount of change in the noise, comprising the steps of:

a) determining an estimate of the covariance matrix $\Lambda$ of the change in the multichannel noise;

b) determining estimates of the covariance terms $N_s$ and j of the existing calibration samples;

c) computing the updated b-vector from said estimates by using formula $\hat{b}=(N_s \pm \Lambda)^+ j$ or a substantially equivalent expression;

whereby a-priori knowledge about said change in the noise can be used to update said existing b-vector regardless of how much knowledge is otherwise available about the signal and the noise.

19. A method as defined in claim 18, further including the step of slope-adjusting said updated b-vector.

* * * * *